United States Patent [19]

Tinney et al.

[11] 4,022,761
[45] May 10, 1977

[54] TRIPEPTIDES AND METHODS FOR THEIR PRODUCTION

[75] Inventors: Francis John Tinney; Ernest D. Nicolaides, both of Ann Arbor; Marland Paul Hutt, Saline; Thomas Frederick Mich, Ann Arbor, all of Mich.

[73] Assignee: Parke, Davis & Company, Detroit, Mich.

[22] Filed: Jan. 19, 1976

[21] Appl. No.: 650,097

[52] U.S. Cl. ............. 260/112.5 LH; 260/112.5 R; 424/177
[51] Int. Cl.² ..................................... C07C 103/52
[58] Field of Search ........... 260/112.5 R, 112.5 LH

[56] References Cited
UNITED STATES PATENTS 3,725,380   4/1973   Konig et al. ................ 260/112.5 R

OTHER PUBLICATIONS

J. M. Stewart and J. D. Young, "Solid Phase Peptide Synthesis," Freeman and Co., San Francisco, 1969, pp. 9–13.
J. D. Roberts and M. C. Caserio, "Basic Principles of Organic Chemistry," Benjamin, Inc., New York, 1965, p. 564.
E. Schroder and K. Lubke, "The Peptides," vol. 1, Academic Press, New York, 1965, pp. 108–111.

Primary Examiner—Delbert R. Phillips
Attorney, Agent, or Firm—Stephen Raines; George M. Richards; David B. Ehrlinger

[57] ABSTRACT

New tripeptides having the formula A-$R_1$-Ser(benzyl)-Tyr (benzyl)-$R_2$ wherein A is t-butoxycarbonyl or cyclohexyl carbonyl, $R_1$ is Trp, His(benzyl), Cys(benzyl) or Pro and $R_2$ is lower alkoxy, hydrazino, amino, lower alkylamino, di(lower alkyl)amino, benzylamino, allylamino, (diethoxyphosphinyl)methylamino, 2-(diethoxyphosphinyl)ethylamino or 2-[[(phenylmethyl)amino]sulfonyl]ethylamino, methods for their production, and the use of said tripeptides as luteinizing hormone releasing factor antagonists.

5 Claims, No Drawings

TRIPEPTIDES AND METHODS FOR THEIR PRODUCTION

SUMMARY AND DETAILED DESCRIPTION

The present invention relates to new peptide compounds that are useful as luteinizing hormone releasing factor antagonists and to methods for their production. More particularly, the invention relates to new N-protected tripeptides that are represented by the formula

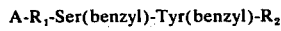

A-R₁-Ser(benzyl)-Tyr(benzyl)-R₂    I wherein A is t-butoxycarbonyl or cyclohexylcarbonyl, R₁ is Trp, His(benzyl), Cys(benzyl) or Pro and R₂ is lower alkoxy, hydrazino, amino, lower alkylamino, di(lower alkyl)amino, benzylamino, allylamino, (diethoxyphosphinyl)methylamino, 2-(diethoxyphosphinyl)ethylamino or 2-[[(phenylmethyl)amino]-sulfonyl]ethylamino.

In formula I, the conventional symbols for amino acid residues of peptide compounds are used and each is intended to have the following meaning: Trp, L-tryptophyl; His(benzyl), N$^{im}$-benzyl-L-histidyl; Cys(benzyl), S-benzyl-L-cysteinyl; Pro, L-prolyl; Tyr(benzyl), O-benzyl-L-tyrosyl and Ser(benzyl), O-benzyl-L-seryl. In addition, the term lower alkyl is intended to mean a straight, branched or cyclic saturated hydrocarbon moiety of up to six carbon atoms, such as methyl, ethyl, isopropyl and cyclopropyl and lower alkoxy is intended to mean an alkoxy group having a straight, branched or cyclic saturated hydrocarbon moiety of up to six carbon atoms, such as methoxy, ethoxy and isopropoxy. These symbols and terms will also be used in the formulae that follow for other compounds and each such symbol or term should be understood to have the meaning given above.

In accordance with this invention, compounds of the formula I, wherein A and R₁ are as previously defined and R₂ is lower alkoxy, are produced by removing a protected tripeptide from a resin complex of the following structure

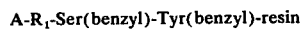

A-R₁-Ser(benzyl)-Tyr(benzyl)-resin    II wherein said resin is a resin employed in solid phase peptide syntheses, such as those disclosed in a text by Stewart and Young, "Solid Phase Peptide Synthesis," W. H. Freeman & Company, San Francisco, 1969, which is incorporated by reference, preferably the resin is a cross-linked copolymer comprising 98 to 99 percent polystyrene cross-linked with 1 to 2 percent divinylbenzene, which is attached to the protected tripeptide through a methyleneoxy bridge wherein the methylene group is attached to the polymeric portion of the resin and the oxygen atom is attached to the protected tripeptide and A and R₁ are as previously defined; by treating said resin of the formula II with a lower alkyl alcohol in the presence of tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

While it is not a preferred procedure, compounds of thd formula I wherein R₂ is hydrazino, amino, lower alkylamino, di(lower alkyl)amino, benzylamino or allylamino may be prepared by reacting compounds of the formula II wherein A and R₁ are as previously defined, with hydrazine, ammonia, lower alkylamine, di(lower alkyl)amine, benzylamine or allylamine.

The resin complex is suspended in a solvent, such as methanol, ethanol, dimethylformamide, etc., at a temperature of from about 0° C. to 50° C. for periods of from 12 hours to 10 days. When employing less reactive amines, the preferred solvent is dimethylformamide.

The complex resins of the formula II are prepared by coupling a protected amino acid of the formula

A—R₁—OH    III wherein A and R₁ are as previously defined, with a complex resin of the formula

Ser(benzyl)-Tyr(benzyl)-resin    IV in an organic solvent, such as dichloromethane with the aid of dicyclohexylcarbodiimide. The three components may generally be used in about equimolar quantities but excess amounts of the protected amino acid and of dicyclohexylcarbodiimide are sometimes advantageous. The reaction is generally conducted at about room temperature for a period of from about fifteen minutes to about 16 hours.

The complex resins of the formula IV are prepared by treating complex resins of the formula

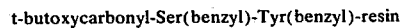

t-butoxycarbonyl-Ser(benzyl)-Tyr(benzyl)-resin    V with a large excess of trifluoroacetic acid utilizing dichloromethane as the solvent at temperatures of from 20° to 30° C. for about 10 minutes.

The complex resins of formula V are prepared by coupling

t-butoxycarbonyl-Ser(benzyl)—OH to a complex resin of the formula

Tyr(benzyl)-resin    VI using the reaction procedure described for the preparation of compounds of the formula II.

The complex resins of the formula VI are prepared by treating the known complex resins of the formula

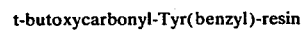

t-butoxycarbonyl-Tyr(benzyl)-resin with trifluoroacetic acid using the reaction procedure for the preparation of compounds of the formula IV.

In accordance with this invention, compounds of the formula I, wherein A and R₁ are as previously described and R₂ is hydrazino, amino, lower alkylamino, di(lower alkyl)-amino, benzylamino or allylamino, are prepared by reacting a compound of the formula I wherein R₂ is alkoxy, preferably methoxy with hydrazine, ammonia, lower alkylamine, di(lower alkylamine), benzylamine or allylamine.

The reactions are conducted at temperatures of from about 5° to 100° C. for from 3 hours to 4 days, preferably about room temperature. Generally, a large excess of hydrazine, preferably used in the form of its hydrate, or amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

In addition, in accordance with this invention, compounds of the formula I, wherein A and $R_1$ are as previously defined and $R_2$ is amino, lower alkylamino, di(lower alkyl)-amino, benzylamino, allylamino, (diethoxyphosphinyl)methylamino, 2-(diethoxyphosphinyl)ethylamino or 2-[[(phenylmethyl)-amino]sulfonyl]ethylamino, are prepared by reacting a compound of the formula

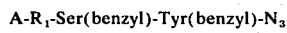

A-$R_1$-Ser(benzyl)-Tyr(benzyl)-$N_3$    VII with ammonia, a lower alkylamine, di(lower alkyl)amine, benzylamine, allylamine, (diethoxyphosphinyl)methylamine, 2-(diethoxyphosphinyl)ethylamine or 2-[[(phenylmethyl)amino]sulfonyl]ethylamine in a non-reactive solvent such as dimethylformamide, dioxane, tetrahydrofuran or mixtures thereof. The reaction is carried out at about −30° C. to about 0° C. for about 12 to 24 hours, preferably −20° C. to 0° C. for from 16 to 19 hours. The two reactants are used in approximately equimolar amounts although a slight excess of amine, about 10 percent is preferred. When A is t-butoxycarbonyl, care should be taken to avoid the presence of an excess of acid.

The azide compounds of the formula VII are normally prepared in situ by reacting a peptide hydrazide compound of the formula I wherein A and $R_1$ are as previously defined and $R_2$ is hydrazino, with a lower alkyl nitrite, preferably isoamyl nitrite in the presence of an acid, preferably hydrochloric acid, in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula I. The preparation of the azide is carried out at a temperature between −30° and 0° C. Following the in situ formation of the azide of formula VII and prior to the further reaction of the peptide azide with the appropriate amine to form certain tripeptides of formula I, a tertiary amine such as triethylamine is added to the reaction mixture to neutralize the acid used.

Compounds of the formula I wherein A and $R_1$ are as previously described and $R_2$ is hydrazino, amino, lower alkylamino, di(lower alkyl)amino, benzylamino, allylamino, (diethoxyphosphinyl)methylamino, 2-(diethoxyphosphinyl)ethylamino or 2-[[(phenylmethyl)amino]sulfonyl]ethylamino are prepared by coupling a compound of the formula

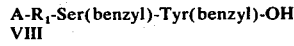

A-$R_1$-Ser(benzyl)-Tyr(benzyl)-OH
VIII with hydrazine, ammonia, lower alkylamine, di(lower alkyl)-amine, benzylamine, allylamine, (diethoxyphosphinyl)methylamine, 2-(diethoxyphosphinyl)ethylamine or 2-[[(phenylmethyl)-amino]sulfonyl]ethylamine in an inert solvent in the presence of dicyclohexylcarbodiimide.

The above reaction is carried out using approximately equivalent amounts of reactants and dicyclohexylcarbodiimide in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° to 50° C., preferably room temperature for periods of from 10 hours to 5 days.

1-Hydroxybenzotriazole may also be used in the above reaction in addition to the dicyclohexylcarbodiimide. The 1-hydroxybenzotriazole is added in a ratio of one to two equivalents when compared to the reactants.

The compounds of the formula VIII are prepared by the hydrolysis of a compound of formula I wherein A and $R_1$ are as previously defined and $R_2$ is lower alkoxy. The reaction is conducted at temperatures of from 20° to 30° C. using about 0.25 ml. of a two normal aqueous sodium hydroxide solution and 10 ml. of solvent for each millimole of ester. The compound of formula VIII is isolated after acidification with aqueous citric acid.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Tripeptides of this invention were screened for LRF antagonist activity in vitro using rat anterior pituitary cell cultures as described by Vale et al. [Endocrinology, 91, 562 (1972)]. The inhibition of LRF (luteinizing hormone release factor) induced luteinizing hormone (LH) release into the culture medium is the endpoint in this in vitro bioassay.

Following are the results of the above tests on certain preferred compounds.

ACTIVITY TABLE FOR IN VITRO TEST IN RAT ANTERIOR PITUITARY CELL CULTURES

| | Molar Conc. | LH Value ng/ml. | % LH Release Inhibition |
|---|---|---|---|
| $N^\alpha$-t-butoxycarbonyl-$N^{im}$-benzyl-L-histidyl-O-benzyl-L-seryl-O-benzyl-L-tyrosine-N-2-[[(phenylmethyl)amino]-sulfonyl]ethylamide | $1 \times 10^{-7}$ $5 \times 10^{-7}$ | 30.30 17.13 | 24 67 |
| LRF control | $5 \times 10^{-10}$ | 56.00 | |
| Saline control | | 7.09 | |
| | $1 \times 10^{-6}$ | 10.31 | 91 |
| LRF control | $2.5 \times 10^{-10}$ | 36.96 | |
| Saline control | | 7.70 | |
| $N^\alpha$-t-butoxycarbonyl-$N^{im}$-benzyl-L-histidyl-O-benzyl-L-seryl-O-benzyl-O-tyrosine, N-isopropylamide | $5 \times 10^{-7}$ $1 \times 10^{-7}$ $5 \times 10^{-8}$ | 28.48 49.65 45.54 | 58 13 22 |
| LRF control | $5 \times 10^{-10}$ | 56.00 | |
| Saline control | | 8.90 | |
| | $1 \times 10^{-6}$ | 12.65 | 86 |
| LRF control | $1 \times 10^{-9}$ | 33.10 | |
| Saline control | | 9.33 | |
| $N^\alpha$-t-butoxycarbonyl-$N^{im}$-benzyl-L-histidyl-O-benzyl-L-seryl-O-benzyl-L-tyrosine N,N-dimethylamide | $1 \times 10^{-6}$ $6 \times 10^{-7}$ $3 \times 10^{-7}$ $1 \times 10^{-7}$ $6 \times 10^{-8}$ | 16.18 12.55 14.95 16.47 25.78 | 69 83 74 68 31 |
| LRF control | $3.5 \times 10^{-10}$ | 33.78 | |
| Saline control | | 8.33 | |
| | $1 \times 10^{-6}$ $1 \times 10^{-7}$ | 7.85 23.31 | 98 36 |
| LRF control | $3.5 \times 10^{-10}$ | 32.06 | |
| Saline control | | 7.43 | |
| | $1 \times 10^{-6}$ | 15.79 | 90 |
| LRF control | $2.5 \times 10^{-10}$ | 50.25 | |
| Saline control | | 11.96 | |
| $N^\alpha$-t-butoxycarbonyl-$N^{im}$-benzyl-L-histidyl-O-benzyl- L-seryl-O-benzyl-L-tyrosine N-2-(diethoxyphosphinyl)- | $1 \times 10^{-6}$ $3.5 \times 10^{-7}$ $1 \times 10^{-7}$ $3.5 \times 10^{-8}$ | 10.65 10.87 16.02 25.87 | 104 103 84 47 |

| | Molar Conc. | LH Value ng/ml. | % LH Release Inhibition |
|---|---|---|---|
| ethylamide | $1 \times 10^{-8}$ | 33.70 | 18 |
| LRF Control | $5 \times 10^{-10}$ | 38.48 | |
| Saline Control | | 11.59 | |
| | $1 \times 10^{-6}$ | 15.40 | 86 |
| LRF control | $3.5 \times 10^{-10}$ | 47.67 | |
| Saline control | | 10.16 | |

The luteinizing hormone releasing factor (LRF) is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH—RH, and its biological activity, see Science, Vol. 174, No. 4008, Oct. 29, 1971, pages 511–512. Thus, the tripeptides of this invention are useful in controlling ovulation and in restricting fertility.

The invention is illustrated by the following examples.

EXAMPLE 1

$N^\alpha$-t-Butoxycarbonyl-$N^{im}$benzyl-L-histidyl-O-benzyl-L-seryl-O-benzyl-L-tyrosine methyl ester A mixture of 100 g. of chloromethylated polystyrene resin having 1.16 mmole of chlorine per gram, and 64.6 g. (0.174 mole) of $N^\alpha$-t-butoxycarbonyl-O-benzyl-L-tyrosine in one liter of ethanol is treated with 16.3 g. (0.116 mol) of triethylamine and refluxed for 3 days. The resin is separated by filtration, washed with ethanol, water, methanol, dichloromethane and ether, successively, and then dried overnight at 40° C. giving the $N^\alpha$-t-butoxycarbonyl-O-benzyl-L-tyrosine resin (113 g.).

A tubular flask of 400 ml. capacity, having a sintered glass disc and stopcock at one end and a suitably placed opening for addition of materials at the other is clamped to a motor which imparts a rocking motion to the flask. The flask is charged with 33.3 g. (20 mmol) of $N^\alpha$-t-butoxycarbonyl-O-benzyl-L-tyrosine resin and 200 ml. of dichloromethane and agitated for ½ hour. The liquid is then drained from the flask by connecting a suction, through a trap, to the stopcock. The resin is retained in the flask by means of the sintered glass disc. The $N^\alpha$-t-butoxycarbonyl protecting group is removed by rocking the resin with 100 ml. of trifluoroacetic acid and 150 ml. of dichloromethane for ten minutes. The liquid is drained from the flask and the trifluoroacetate salt of O-benzyl-L-tyrosine resin is washed three times with 250 ml. of dichloromethane each time. The trifluoroacetate salt of the O-benzyl-L-tyrosine resin is converted to O-benzyl-L-tyrosine resin by the addition of 30 ml. of triethylamine in 250 ml. of cold dichloromethane and rocking the reaction for 5 minutes. The flask is drained and the resin again washed three times with 250 ml. of dichloromethane each time. The O-benzyl-L-serine moiety is coupled to the O-benzyl-L-tyrosine resin by adding 7.09 g. (24 mmol) of $N^\alpha$-t-butoxycarbonyl-O-benzyl-L-serine in 100 ml. of dichloromethane, shaking for 30 minutes, adding 4.94 g. (24 mmol) of dicyclohexylcarbodiimide in 50 ml. of dichloromethane and rocking the reaction flask for four hours. The flask is drained and the resin washed 3 times with 250 ml. of dichloromethane each time. Trifluoroacetic acid (100 ml.) and dichloromethane (150 ml.) are used as above to remove the t-butoxycarbonyl protecting group and the resin drained and washed as before. Triethylamine, 30 ml. in 250 ml. of cold dichloromethane, is used to liberate the O-benzyl-L-seryl-O-benzyl-L-tyrosine resin, which is treated with 8.29 g. (24 mmol) of $N^\alpha$-t-butoxycarbonyl-$N^{im}$-benzyl-L-histidine in 100 ml. of dichloromethane, rocked for thirty minutes and 4.94 g. (24 mmol) of dicyclohexylcarbodiimide added in 50 ml. of dichloromethane. The coupling reaction is rocked for four hours, the flask drained and the resin washed two times with 250 ml. of dichloromethane each time. The resin is then washed with 150 ml. of ethanol, agitated for 20 minutes, and poured out of the flask on a filter funnel where it is washed with ethanol and then with ether and then dried at 50° C. and under reduced pressure.

The dried resin is stirred overnight with 50 ml. of triethylamine and 500 ml. of methanol, removed by filtration and the filtrate evaporated to yield crude $N^\alpha$-t-butoxycarbonyl-$N^{im}$-benzyl-L-histidyl-O-benzyl-L-seryl-O-benzyl-L-tyrosine methyl ester. The product is let stand overnight in isopropyl ether, filtered and washed with diethyl ether. The product melts at 101°–103° C.

The general procedure and equipment for solid phase peptide synthesis is described by Steward and Young, "Solid Phase Peptide Synthesis," W. H. Freeman and Company, San Francisco, 1969.

EXAMPLE 2

$N^\alpha$-t-Butoxycarbonyl-$N^{im}$-benzyl-L-histidyl-O-benzyl-L-seryl-O-benzyl-L-tyrosine N-ethylamide $N^\alpha$-t-butoxycarbonyl-$N^{im}$-benzyl-L-histidyl-O-benzyl-L-seryl-O-benzyl-L-tyrosine methyl ester, 0.3 g., is dissolved in 150 ml. of methanol and an excess of ethylamine added. The solution is allowed to stand at room temperature in a closed vessel for 3 days. The solvent is evaporated and the resulting crude product purified by column chromatography on silica gel using chloroform-methanol-water (60:30:5) to give 0.2 g. as a hemihydrate; ultraviolet in methanol $\lambda$ 283 $E_1^1$ 16.4; $\lambda$ 276 $E_1^1$ 19.3.

EXAMPLE 3

$N^\alpha$-t-Butoxycarbonyl-$N^{im}$-benzyl-L-histidyl-O-benzyl-L-seryl-O-benzyl-L-tyrosine N-benzylamide $N^\alpha$-t-Butoxycarbonyl-$N^{im}$-benzyl-L-histidyl-O-benzyl-L-seryl-O-benzyl-L-tyrosine methyl ester, 395 mg., is dissolved in 20 ml. of methanol and treated with 0.55 ml. (10 fold molar excess) of benzylamine. The reaction is allowed to stand for four days. A large excess of benzylamine, 5 ml., is added and the reaction let stand for 7 days. At the end of this time, the mixture is evaporated and the residual oil treated with ether and let stand for 3 days. The product is then separated by filtration, washed with ether and dried at 50° C.; 250 mg. as a hemi-hydrate; m.p. 138°–140° C.

EXAMPLE 4

$N^\alpha$-t-Butoxycarbonyl-$N^{im}$-benzyl-L-histidyl-O-benzyl-L-seryl-O-benzyl-L-tyrosine N-cyclopropylamide $N^\alpha$-t-Butoxycarbonyl-$N^{im}$-histidyl-O-benzyl-L-seryl-O-benzyl-L-tyrosine methyl ester, 395 mg., is dissolved in 20 ml. of methanol and treated with 0.5 ml. of cyclopropylamine. The reaction is let stand for 4 days, 5 ml. of cyclopropylamine added and the reaction let stand for 7 days. The mixture is then evaporated, the residue triturated with ether, filtered and the solid dried at 40° C. under reduced pressure; 132 mg. as a monohydrate; m.p. 147°–149° C.

EXAMPLE 5

$N^\alpha$-t-Butoxycarbonyl-$N^{im}$-benzyl-L-histidyl-O-benzyl-L-seryl-O-benzyl-L-tyrosine N-allylamide $N^\alpha$-t-Butoxycarbonyl-$N^{im}$-benzyl-L-histidyl-O-benzyl-L-seryl-O-benzyl-L-tyrosine methyl ester, 395 mg., is dissolved in 10 ml. by warming and treated with 5 ml. of allylamine. The reaction is let stand for seven days. The mixture is then evaporated to a crude solid which is triturated with ether and filtered. The solid product weighs 63 mg. as a monohydrate; m.p. 130°–132° C.

EXAMPLE 6

$N^\alpha$-t-Butoxycarbonyl-$N^{im}$-benzyl-L-histidyl-O-benzyl-L-seryl-O-benzyl-L-tyrosine N-isopropylamide $N^\alpha$-t-Butoxycarbonyl-$N^{im}$-benzyl-L-histidyl-O-benzyl-L-seryl-O-benzyl-L-tyrosine, 310 mg. is dissolved in 25 ml. of tetrahydrofuran and treated with 0.35 ml. of isopropylamine, 54 mg. of 1-hydroxybenzotriazole and 87 mg. of dicyclohexylcarbodiimide. The reaction is stirred for 1 hour with cooling and then at room temperature for 3 days. The mixture is then evaporated to dryness and the residue chromatographed over silica gel in chloroform-methanol (4:1). The product from the eluate was separated from a small amount of insoluble material in ether solution and precipitated by the addition of hexane to the ether solution; 118 mg.; m.p. 131°–133° C.

The methyl ester of $N^\alpha$-t-butoxycarbonyl-$N^{im}$-benzyl-L-histidyl-O-benzyl-L-seryl-O-benzyl-L-tyrosine [7.2 g. (9 mmoles)], methanol (100 ml.), and a two normal sodium hydroxide solution (5 ml. - 10 mmoles) are stirred for 3 hours at ambient temperature followed by the addition of 100 ml. of water in portions. The reaction mixture becomes cloudy indicating incomplete hydrolysis. The mixture is refrigerated overnight. 2.5 ml. (5 mmoles) of two normal sodium hydroxide solution is added and the mixture stirred for half an hour. After the addition of 50 ml. of water, the solution remains clear. The reaction mixture is filtered, the filtrate is acidified with 1.5 g. (8 mmoles, 16 meq.) of citric acid. The solution is decanted and concentrated. The combined insoluble materials are washed with water and dried. The product is recrystallized from ethanol and water yielding 3.18 g. of acid, m.p. 172°–175° C. (dec.). An additional 0.78 g. is obtained by concentration of the filtrate; $[\alpha]_D^{25}$ −1.9° (c 1.035).

EXAMPLE 7

$N^\alpha$-t-Butoxycarbonyl-$N^{im}$-benzyl-L-histidyl-O-benzyl-L-seryl-O-benzyl-L-tyrosyl hydrazide $N^\alpha$-t-Butoxycarbonyl-$N^{im}$-benzyl-L-histidyl-O-benzyl-L-seryl-O-benzyl-L-tyrosine methyl ester, obtained as crude product from methanolysis of the solid phase peptide preparation is dissolved in tetrahydrofuran and treated with an excess of hydrazine hydrate. The solution is stirred for three days, evaporated to dryness and the residue stirred with water for several hours, filtered and the solid washed with water and dried at 50° C. The product is $N^\alpha$-t-butoxycarbonyl-$N^{im}$-benzyl-L-histidyl-O-benzyl-L-seryl-O-benzyl-L-tyrosyl hydrazide $[\alpha]_D^{25}$ −16°. The hydrazide can be crystallized from ethanol-water (1:1); m.p. 132°–136° C.

EXAMPLE 8

$N^\alpha$-t-Butoxycarbonyl-$N^{im}$-benzyl-L-histidyl-O-benzyl-L-seryl-O-benzyl-L-tyrosine 2-[[(phenylmethyl)amino]-sulfonyl]ethylamide $N^\alpha$-t-Butoxycarbonyl-$N^{im}$-benzyl-L-histidyl-O-benzyl-L-seryl-O-benzyl-L-tyrosyl hydrazide, 400 mg., is dissolved in 10 ml. of dimethylformamide, cooled to −20° C., treated with 0.6 ml. of 2.5 N hydrogen chloride in tetrahydrofuran, then with 0.14 ml. of isopentylnitrite and stirred at −20° C. during 1 hour. The reaction is cooled to −40°, treated with 0.30 ml. of triethylamine, cooled to −50°, and 125 mg. of taurine N-benzylamide hydrochloride salt added and the reaction stirred to 0° during 1 hour and held at 0° for 19 hours. The reaction mixture is filtered and the filtrate evaporated. The residue is triturated with ether, dissolved in ethyl acetate and precipitated with hexane and triturated with water. The product is finally crystallized from ethanol-water; 230 mg. as a hemihydrate; m.p. 93°–96°.

EXAMPLE 9

$N^\alpha$-t-Butoxycarbonyl-$N^{im}$-benzyl-L-histidyl-O-benzyl-L-seryl-O-benzyl-L-tyrosine N-(diethoxyphosphinyl)methylamide $N^\alpha$-t-Butoxycarbonyl-$N^{im}$-benzyl-L-histidyl-O-benzyl-L-seryl-O-benzyl-L-tyrosyl hydrazide, 560 mg., is dissolved in 15 ml. of dimethylformamide and the solution cooled to −25° C. Hydrogen chloride, 2.82N in tetrahydrofuran, 0.75 ml., is added followed by 0.11 ml. of isopentylnitrite (90%). The solution is stirred at −25° to −30° C. for one hour, the temperature lowered to −50° C. and 0.44 ml. of triethylamine added, followed by 204 mg. of (diethoxyphosphinyl)methylamine hydrochloride in 2 ml. of dimethylformamide. The mixture is stirred while warming to 0° C. during 1 hour and held at 0° C. overnight. The solution is evaporated and the residue chromatographed over silica gel using benzene:methanol (2:1) for elution. A second chromatography over silica gel using chloroform with increasing amounts of methanol (2 to 10%) provides homogeneous material in center fractions as demonstrated by thin layer chromatography. The selected fractions are evaporated and the residue dissolved in ether and precipitated with pentane to give the product as a white solid which is dried at 40° C. under reduced pressure; 276 mg.; $[\alpha]_D^{25}$ −5.8° (c 1.03, methanol).

Diethyl aminomethylphosphonate hydrochloride is prepared by stirring a solution of 2.97 g. of diethyl phthalimidomethylphosphonate, 1 ml. of hydrazine hydrate and 100 ml. of absolute ethanol at room temperature for 48 hours. The precipitate is separated by filtration and the ethanol removed from the filtrate under reduced pressure. The residue is treated with cold 0.5N hydrochloric acid and filtered. The filtrate is lyophilized to a gum which is dissolved in water and extracted with chloroform. Lyophilization again gives a gum which is chromatographed on silica gel with benzene-methanol (2:1). The product is recovered by evaporation of the fractions and lyophilization from water. The material may be further purified by solution in methanol and filtering, evaporating, dissolving in water and lyophilizing.

Diethyl phthalimidomethylphosphonate is prepared by the procedure described in *J. Org. Chem.*, 36, 1379 (1971) for the dimethyl phthalimidomethylphosphonate. A mixture of 24 g. of bromomethylphthalimide, 18.3 g. of triethylphosphite and 100 ml. of xylene is heated and stirred at reflux for 5 hours. Ethyl bromide is allowed to escape through the condenser. The xylene is removed under reduced pressure to give a yellow oil which on addition of ether and pentane affords crystals; 23.7 g.; m.p. 60°–61° C.

EXAMPLE 10

$N^\alpha$ -t-Butoxycarbonyl-$N^{im}$-benzyl-L-histidyl-O-benzyl-L-seryl-O-benzyl-L-tyrosine, N,N-dimethylamide A solution of 560 mg. of $N^\alpha$ -t-butoxycarbonyl-$N^{im}$-benzyl-L-histidyl-O-benzyl-L-seryl-O-benzyl-L-tyrosyl hydrazide in 15 ml. of dimethylformamide is cooled to $-25°$ C. and treated with 0.75 ml. of 2.82N hydrogen chloride in tetrahydrofuran followed by addition of 0.11 ml. of isopentylnitrite (90%). The solution is stirred at $-25°$ to $-30°$ C. for 1 hour and then cooled to $-50°$ C. and treated with 0.44 ml. of triethylamine followed by 202 mg. of dimethylamine hydrochloride in 2 ml. of dimethylformamide. The mixture is stirred while warming to 0° C. during 1 hour and held at 0° C. overnight. The dimethylformamide is removed by evaporation under reduced pressure and at 45° C. The residue is chromatographed twice on silica gel, first with benzene-methanol (2:1) and then with chloroform-methanol (98 to 90: 2 to 10) and then is precipitated from ether-pentane to yield 259 mg.; $[\alpha]_D^{25}$ $-12.1°$ (c 1.0, DMF).

EXAMPLE 11

$N^\alpha$ -Cyclohexylcarbonyl-$N^{im}$-benzyl-L-histidyl-O-benzyl-L-seryl-O-benzyl-L-tyrosyl hydrazide $N^\alpha$ -Cyclohexylcarbonyl-$N^{im}$-benzyl-L-histidyl-O-benzyl-L-seryl-O-benzyl-L-tyrosine methyl ester, 0.3 g., is dissolved in 200 ml. of methanol and treated with 1 g. of hydrazine hydrate. The reaction is let stand at room temperature for two days. The solvent is removed under reduced pressure and the residue chromatographed in silica gel using chloroform-methanol-water (60:30:5) to yield 0.15 g. as a hemihydrate; m.p. 145°–150° C.

$N^\alpha$ -Cyclohexylcarbonyl-$N^{im}$-benzyl-L-histidyl-O-benzyl-L-seryl-O-benzyl-L-tyrosine methyl ester is obtained from $N^\alpha$ -t-butoxycarbonyl-$N^{im}$-benzyl-L-histidyl-O-benzyl-L-seryl-O-benzyl-L-tyrosine resin by washing 6.1 g. of the resin two times with 200 ml. of dichloromethane, deblocking with 50% trifluoroacetic acid in dichloromethane for ½ hour, washing with 200 ml. of dichloromethane five times; neutralizing with 200 ml. of 10% triethylamine in dichloromethane for fifteen minutes, washing with 200 ml. of dichloromethane five times; adding 0.8 g. of cyclohexylcarboxylic acid (hexahydrobenzoic acid) and equilibrating with 20 ml. of dimethylformamide and 180 ml. of dichloromethane during one hour; adding 1.2 g. of dicyclohexylcarbodiimide in 20 ml. of dichloromethane and agitating the reaction overnight. The resin is drained and washed with 200 ml. of dichloromethane five times. The resin, 4.7 g., is suspended in 300 ml. of methanol and 30 ml. of triethylamine and stirred for two days at room temperature. The mixture is filtered and the filtrate evaporated. The residue is chromatographed on silica gel using chloroform-methanol-water (60:30:5); m.p. 128°–131°.

EXAMPLE 12

$N^\alpha$ -Cyclohexylcarbonyl-$N^{im}$-benzyl-L-histidyl-O-benzyl-L-seryl-O-benzyl-L-tyrosine N-ethylamide $N^\alpha$ -Cyclohexylcarbonyl-$N^{im}$-benzyl-L-histidyl-O-benzyl-L-seryl-O-benzyl-L-tyrosine methyl ester, 0.3 g., is dissolved in 200 ml. of methanol and 10 ml. of ethylamine and let stand at room temperature for 4 days. The solvent is removed under reduced pressure and the residue chromatographed on silica gel using chloroform-methanol-water (60:30:5) to yield 0.22 g. as a hemihydrate; m.p. 160°–165° C.

EXAMPLE 13

$N^\alpha$ -t-Butoxycarbonyl-L-tryptophyl-O-benzyl-L-seryl-O-benzyl-L-tyrosyl hydrazide $N^\alpha$ -t-Butoxycarbonyl-L-tryptophyl-O-benzyl-L-seryl-O-benzyl-L-tyrosine methyl ester, 300 mg., is dissolved in 10 ml. of ethanol and treated with 1 ml. of hydrazine hydrate. The solution is warmed at 50° C. for 15 minutes and let stand at room temperature overnight. The precipitated white solid is separated by filtration, washed with ethanol and ether and dried; 220 mg., m.p. 166°–168° C.

$N^\alpha$ -t-Butoxycarbonyl-L-tryptophyl-O-benzyl-L-seryl-O-benzyl-L-tyrosine methyl ester is obtained by stirring 5 g. of $N^\alpha$ -t-butoxycarbonyl-L-tryptophyl-O-benzyl-L-seryl-O-benzyl-L-tyrosine resin overnight at room temperature with 150 ml. of methanol and 10 ml. of triethylamine. The mixture is then filtered and evaporated to an oil which solidifies on standing. The product is crystallized from isopropanol as a white solid, 700 mg., m.p. 127°–128° C.

$N^\alpha$ -t-Butoxycarbonyl-L-tryptophyl-O-benzyl-L-seryl-O-benzyl-L-tyrosine resin is obtained by utilizing the solid phase procedure. $N^\alpha$ -t-Butoxycarbonyl-O-benzyl-L-tyrosine resin, 40 g., is deblocked and treated with 10 g. of $N^\alpha$ -t-butoxycarbonyl-O-benzyl-L-serine and the resulting $N^\alpha$ -t-butoxycarbonyl-O-benzyl-L-seryl-O-benzyl-L-tyrosine resin deblocked and treated with 10 g. of $N^\alpha$ -t-butoxycarbonyl-L-tryptophan. Each cycle follows the scheme:

1. 300 ml. of 50% trifluoroacetic acid in dichloromethane.
2. Three washings with 250 ml. of dichloromethane.
3. 250 ml. of cold 10% triethylamine in dichloromethane.
4. Three washings with 250 ml. of dichloromethane
5. Thirty minutes agitation with the $N^\alpha$ -t-butoxycarbonyl amino acid in 250 ml. of dichloromethane.
6. Addition of 7 g. of dicyclohexylcarbodiimide in chloroform with agitation for four to eighteen hours.
7. Three washings with 250 ml. of dichloromethane. The resin is then washed with ethanol and dried.

$N^\alpha$ -t-Butoxycarbonyl-O-benzyl-L-tyrosine resin is obtained by mixing 40 g. of chloromethylated resin (1.0 mmoles of chlorine per gram), 20 g. of $N^\alpha$ -t-butoxycarbonyl-O-benzyl-L-tyrosine and 5.5 g. of triethylamine in 500 ml. of absolute ethanol. The mixture is stirred for 2 days at room temperature, filtered, the resin washed with ethanol and ether, and dried; 49 g. Analysis for nitrogen shows 0.72 mmoles per gram.

EXAMPLE 14

$N^\alpha$-t-Butoxycarbonyl-$N^{im}$-benzyl-L-histidyl-O-benzyl-L-seryl-O-benzyl-L-tyrosine N-2-(diethoxyphosphinyl)ethylamide A solution of 1.303 g. (1.6 mmol) of $N^\alpha$-t-butoxycarbonyl-$N^{im}$-benzyl-L-histidyl-O-benzyl-L-seryl-O-benzyl-L-tyrosyl hydrazide in 30 ml. of dimethylformamide is cooled to −15° C. and treated with 1.88 ml. (4.8 mmol) of 2.55 N hydrogen chloride in tetrahydrofuran. The mixture is then treated with 0.26 ml. (1.92 mmol) of isopentylnitrite and held at −20° C. for 1 hour with stirring. The reaction mixture is then cooled to −35° C. and treated with 0.94 ml. (6.7 mmol) of triethylamine and then with 0.348 g. (1.6 mmol) of 2-(diethoxyphosphinyl)ethylamine hydrochloride. The reaction mixture is stirred for one and a half hours while the temperature is raised to 0° C. and then held at 0° C. overnight and evaporated to dryness. The residue is triturated with boiling ethyl acetate and filtered. The filtrate is washed with saturated sodium bicarbonate solution and with salt solution, dried over magnesium sulfate and evaporated to a glassy solid. The product is triturated with n-hexane and dried to a gummy solid, 520 mg., which is purified by chromatography over 20 g. of silica gel with chloroform-methanol (4:1). Fractions, selected on the basis of thin layer chromatography, are combined and the solvent evaporated. The residual solid is triturated with n-hexane, filtered and dried; 193 mg., $[\alpha]_D^{25}$ + 13.3° (c 0.99, DMF).

2-(Diethoxyphosphinyl)ethylamine hydrochloride is obtained by treating an ether solution of its free base (J. Org. Chem., 37, 4399 (1972)) with hydrogen chloride in ether, collecting the solid product and drying.

EXAMPLE 15

$N^\alpha$-t-Butoxycarbonyl-$N^{im}$-benzyl-L-histidyl-O-benzyl-L-seryl-O-benzyl-L-tyrosinamide The dried tripeptide resin is added to a cold 10° C. solution of 150 ml. of methanol saturated with gaseous ammonia. The flask is tightly stoppered and the mixture is stirred for 2 days at room temperature. The flask is then cooled, opened, and the mixture filtered. The resin is washed with 50 ml. of hot dimethylformamide and the combined filtrate is evaporated. The ether is added affording the tripeptide amide.

EXAMPLE 16

$N^\alpha$-t-Butoxycarbonyl-$N^{im}$-benzyl-L-histidyl-O-benzyl-L-seryl-O-benzyl-L-tyrosyl hydrazide $N^\alpha$-t-Butoxycarbonyl-$N^{im}$-benzyl-L-histidyl-O-benzyl-L-seryl-O-benzyl-L-tyrosine methyl ester, 0.3 g., 0.38 mmol, is dissolved in 100 ml. of methanol and treated with an excess, 1 g. of hydrazine hydrate. The reaction is let stand at room temperature for 2 days and the solvent is then evaporated and the residue chromatographed on silica gel, using chloroform-methanol-water (60:30:5), to yield 0.2 g. as a hemi-hydrate, m.p. 105°–110° C.

EXAMPLE 17

$N^\alpha$-Cyclohexylcarbonyl-L-tryptophyl-O-benzyl-L-seryl-O-benzyl-L-tyrosine methyl ester $N^\alpha$-t-Butoxycarbonyl-L-tryptophyl-O-benzyl-L-seryl-O-benzyl-L-tyrosine methyl ester is prepared from 40 g. (29 mmol) of $N^\alpha$-t-butoxycarbonyl-O-benzyl-L-tyrosine resin by successive couplings according to the solid-phase procedure with 1) 10 g. of $N^\alpha$-butoxycarbonyl-O-benzyl-L-serine (33 mmol) and 7 g. (34 mmol) of dicyclohexycarbodiimide, 2) 10 g. (33 mmol) of $N^\alpha$-t-butoxycarbonyl-L-tryptophan and 7 g. of dicyclohexylcarbodiimide. The resulting resin, 44 g., is converted to the methyl ester by stirring it overnight at room temperature with 300 ml. of methanol and 30 ml. of triethylamine. The mixture is filtered and the solvent evaporated. The residual oil solidifies and is crystallized from isopropanol to yield 10 g. of white solid, m.p. 130°–131° C.

The methyl ester, 10 g., is dissolved in 50 ml. of trifluoroacetic acid and kept at 20° C. for 15 minutes. The solution is evaporated and the residual oil dissolved in ether. The ether is evaporated and the resulting clear oil taken into 100 ml. of dimethylformamide, cooled to 0° C. and made neutral with triethylamine. The solution is treated with 2 g. of cyclohexane carboxylic acid, 2.1 g. of 1-hydroxybenzotriazole, and 3 g. of dicyclohexylcarbodiimide. The reaction is kept at 4° C. for 48 hours, concentrated to one-half volume, filtered and evaporated to an oil. The oil is washed with ether and solidified from cold isopropanol. The solid is crystallized twice from isopropanol to yield 6 g., m.p. 167°–168° C.

EXAMPLE 18

$N^\alpha$-Cyclohexylcarbonyl-L-tryptophyl-O-benzyl-L-seryl-O-benzyl-L-tyrosyl hydrazide $N^\alpha$-Cyclohexylcarbonyl-L-tryptophyl-O-benzyl-L-seryl-O-benzyl-L-tyrosine methyl ester, 5 g., is dissolved in 75 ml. of ethanol and treated with 7 ml. of hydrazine hydrate. The solution is warmed to 50° C. for 30 minutes and let stand for three days at room temperature. The solid is separated by filtration and washed with ethanol and with ether to yield 4 g., m.p. 204°–205° C.

We claim:

1. A tripeptide represented by the formula

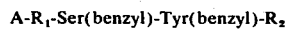

wherein A is t-butoxycarbonyl or cyclohexylcarbonyl, $R_1$ is Trp, His(benzyl), Cys(benzyl) or Pro and $R_2$ is lower alkoxy, hydrazino, amino, lower alkylamino, di(lower alkyl)amino, benzylamino, allylamino, (diethoxyphosphinyl)-methylamino, 2-(diethoxyphosphinyl)ethylamino or 2-[[(phenylmethyl)amino]sulfonyl]ethylamino.

2. The compound of claim 1 having the name $N^\alpha$-t-butoxycarbonyl-$N^{im}$-benzyl-L-histidyl-O-benzyl-L-seryl-O-benzyl-L-tyrosine N-isopropylamide.

3. The compound of claim 1 having the name $N^\alpha$-t-butoxycarbonyl-$N^{im}$-benzyl-L-histidyl-O-benzyl-L-seryl-O-benzyl-L-tyrosine N,N-dimethylamide.

4. The compound of claim 1 having the name $N^\alpha$-t-butoxycarbonyl-$N^{im}$-benzyl-L-histidyl-O-benzyl-L-seryl-O-benzyl-L-tyrosine N-(2-[[(phenylmethyl)]amino]sulfonyl)-ethylamide.

5. The compound of claim 1 having the name $N^\alpha$-t-butoxycarbonyl-$N^{im}$-benzyl-L-histidyl-O-benzyl-L-seryl-O-benzyl-L-tyrosine N-2-(diethoxyphosphinyl)ethylamide.

* * * * *